US005578829A

United States Patent [19]

Talasek et al.

[11] Patent Number: 5,578,829

[45] Date of Patent: Nov. 26, 1996

[54] ON-LINE MONITOR FOR MOISTURE CONTAMINATION IN HCL GAS AND COPPER CONTAMINATION IN $NH_4OH$ SOLUTIONS

[75] Inventors: Robert T. Talasek, Plano; Jeremiah D. Hogan, Dallas, both of Tex.

[73] Assignee: Texas Instruments Incorporated, Dallas, Tex.

[21] Appl. No.: 247,441

[22] Filed: May 23, 1994

[51] Int. Cl.[6] .................... G01N 21/17

[52] U.S. Cl. .................... 250/343; 250/373

[58] Field of Search .................... 250/343, 373, 250/339.10, 339.12, 339.13; 356/436, 437

[56] References Cited

U.S. PATENT DOCUMENTS

| | | | |
|---|---|---|---|
| 3,922,551 | 11/1975 | Williams | 250/343 |
| 4,163,899 | 8/1979 | Burough | 250/343 |
| 4,570,069 | 2/1986 | Gager | 250/343 |
| 4,648,396 | 3/1987 | Raemer | 250/343 X |
| 4,707,603 | 11/1987 | Miemelä et al. | 250/343 X |
| 4,785,184 | 11/1988 | Bien et al. | 250/339.12 X |
| 4,958,076 | 9/1990 | Bonne et al. | 250/343 |
| 5,060,508 | 10/1991 | Wong | 250/343 X |

FOREIGN PATENT DOCUMENTS

| | | | |
|---|---|---|---|
| 62101 | 10/1982 | European Pat. Off. | 356/436 |
| 3324606 | 1/1985 | Germany | 356/436 |
| 60-238746 | 11/1985 | Japan | 250/343 |
| 62-105033 | 5/1987 | Japan | 250/343 |
| 63-234158 | 9/1988 | Japan | 250/373 |
| 4-186141 | 7/1992 | Japan | 250/343 |

*Primary Examiner*—Carolyn E. Fields
*Assistant Examiner*—Edward J. Glick
*Attorney, Agent, or Firm*—Paul Hashim; Jim Brady; Richard Donaldson

[57] ABSTRACT

A light beam is passed through a tube containing a material being monitored and a contaminant wherein the light is absorbed by the contaminant or some form of the contaminant to the exclusion of the material being monitored. Since the amount of light passing through the tube is a function of the amount of contaminant in the tube, the amount of light detected at the downstream end of the tube is a function of the amount of contaminant in the material being monitored. The detected light can be used to provide a quantitative indication of the contaminant, to provide an alarm, to shut down the system to which the material being monitored is being delivered or for other purposes. When the material being monitored is HCl gas and the contaminant is moisture, the tube will generally be stainless steel to avoid galvanic effects since the remainder of the pipe system is generally also stainless steel and the light frequency will be from about 1.0 to about 2.0 micrometers which is a range of frequencies selective to water as opposed to HCl gas. When the material being monitored is aqueous ammonium hydroxide and the contaminant is a transition metal, preferably copper, the tube will be formed of a material inert to ammonium hydroxide, preferably a fluoropolymer with perfluoroethane being the preferred fluoropolymer and the light frequency will be from about 275 to about 350 nanometers which is a range of frequencies selective to a copper ammonium complex which is formed as opposed to aqueous ammonium hydroxide.

12 Claims, 1 Drawing Sheet

ON-LINE MONITOR FOR MOISTURE CONTAMINATION IN HCL GAS AND COPPER CONTAMINATION IN $NH_4OH$ SOLUTIONS

BACKGROUND OF THE INVENTION

1. Field of the Invention

This invention relates to on-line monitoring of moisture in HCl gas and copper in $NH_4$ solutions.

2. Brief Description of the Prior Art

There is presently no known technique for monitoring moisture contamination in corrosive gas distribution systems, or for monitoring metallic contamination and principally copper contamination in chemical distribution systems or process baths, without extracting a sample from the system and then performing a laboratory analysis of the extracted sample. It follows that considerable delay can occur between the time the contamination occurs and the time it is discovered since there is no way of knowing that such contamination has occurred at the time of such occurrence. In the past, the discovery of such contamination has generally been indirect, resulting from a physical observation of a diminution in wafer yield in semiconductor processing procedures in either of the above noted situations, or from discovery of corrosion in the distribution system itself in the case of moisture contamination. It is therefore apparent that a system which can detect the above noted problems on-line would provide a great economic advantage.

SUMMARY OF THE INVENTION

In accordance with the present invention, the above described problems are overcome and there are provided systems capable of detecting, on-line, the presence of moisture in an HCl gas line and the presence of a transition metal, principally copper, in aqueous ammonium hydroxide.

Briefly, the above is accomplished generally by passing a light through a tube containing the material being monitored and the contaminant, wherein the light is absorbed by the contaminant or some form of the contaminant to the exclusion of the material being monitored. In this way, the amount of light passing through the tube will be a function of the amount of contaminant in the tube. Accordingly, the amount of light detected at the downstream end of the tube will be a function of the amount of contaminant in the material being monitored. The detected light can be used to provide a quantitative indication of the contaminant, to provide an alarm, to shut down the system to which the material being monitored is being delivered, any combination thereof or for other purposes.

When the material being monitored is HCl gas and the contaminant is moisture (water), the tube will generally be stainless steel to avoid galvanic effects since the remainder of the pipe system is generally also stainless steel. The light wavelength will be from about 1.0 to about 2.0 micrometers, which is a range of wavelengths selective to water as opposed to HCl gas.

When the material being monitored is aqueous ammonium hydroxide and the contaminant is a transition metal, preferably copper, the tube will be formed of a material inert to ammonium hydroxide, preferably a fluoropolymer, with perfluoroethane being the preferred fluoropolymer. The light wavelength will be from about 275 to about 350 nanometers, which is a range of wavelengths selective to a copper ammonium complex which is formed, as opposed to aqueous ammonium hydroxide. It is expected that any transition metal that forms a complex with ammonia will operate as described above and hereinbelow. There should be an excess of $NH_4$ relative to the transition metal with an excess of about ten times be desirable.

DESCRIPTION OF THE PREFERRED EMBODIMENTS

Figure 1:
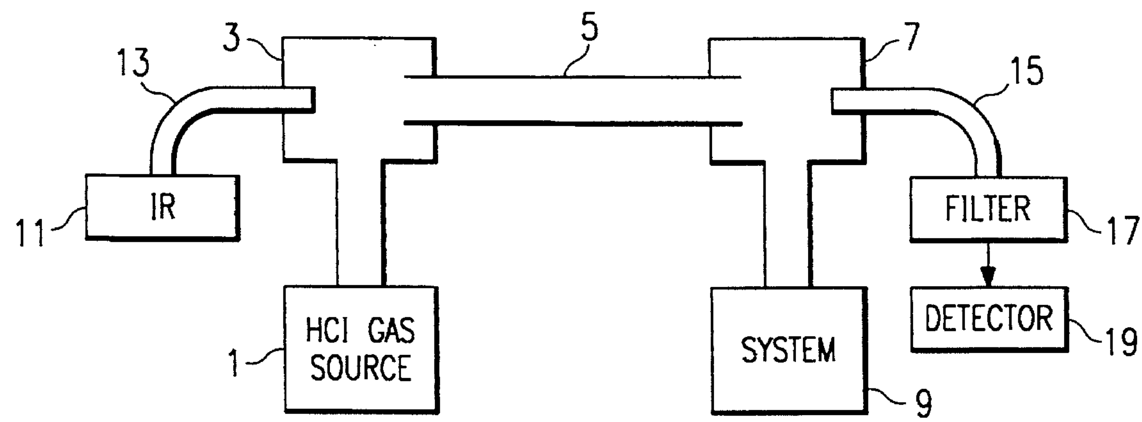
FIG. 1 is a schematic diagram of a monitoring system in accordance with a first embodiment of the invention.

Referring first to FIG. 1, there is a schematic diagram of a system in accordance with the present invention for detecting moisture content in an HCl gas line. HCl gas passes from a HCl gas source 1 through a T-fitting 3 to a first end of a stainless steel pipe 5 secured to the T-fitting 3. The other end of the stainless steel pipe 5 is secured to a T-fitting 7 through which the HCl gas passes, and the HCl gas then travels on to the system 9 wherein the HCl gas will be utilized. The system 9 can be, for example, a semiconductor fabrication operation. The stainless steel pipe 5 is preferably straight so that a light beam entering one end thereof along the pipe axis can exit from the other end unimpeded. Alternatively, or in addition, the interior of the stainless steel pipe 5 is highly reflective, such as by electropolishing, so that light entering one end thereof can being reflected to the other end thereof with minimal absorption.

An infrared source 11 which provides near infrared light having wavelengths in the range of 1 to 2 micrometers (μm) is coupled to the T-fitting 3 via a standard light conducting rod 13 to provide a beam of light passing out of the T-fitting interior and along the axis of the stainless steel pipe 5 to the T-fitting 7 and then to a light conducting rod 15 extending into the T-fitting 7 and along the axis of the stainless steel pipe 5. The light passing through the light conducting rod 15 is filtered by a filter 17 which removes all light having a wavelength below 1 μm. The light passing through the filter 17 impinges upon the detector 19, which cuts off at wavelengths of about 2 μm and above. Accordingly, the filter 17 and detector 19 act as a single band pass filter in the 1 to 2 μm range.

In operation, as gas from the HCl gas source 1 travels to the system 9, it is constantly monitored on-line by the light beam passing from the light conducting rod 13 to the light conducting rod 15. The amount of light reaching the light conducting rod 15 is inversely proportional to the amount of moisture in the stainless steel pipe 5 since the light wavelengths involved are selective to moisture as opposed to HCl gas. The intensity of the light arriving at rod 15 is monitored by the detector 19, the monitor providing, for example, an indication of the amount of moisture in the system with appropriate calibration, an alarm when the amount of moisture in the system exceeds some predetermined value, a shut down of the system 9 when the amount of moisture in the system exceeds some predetermined value, and the like.

Figure 2:
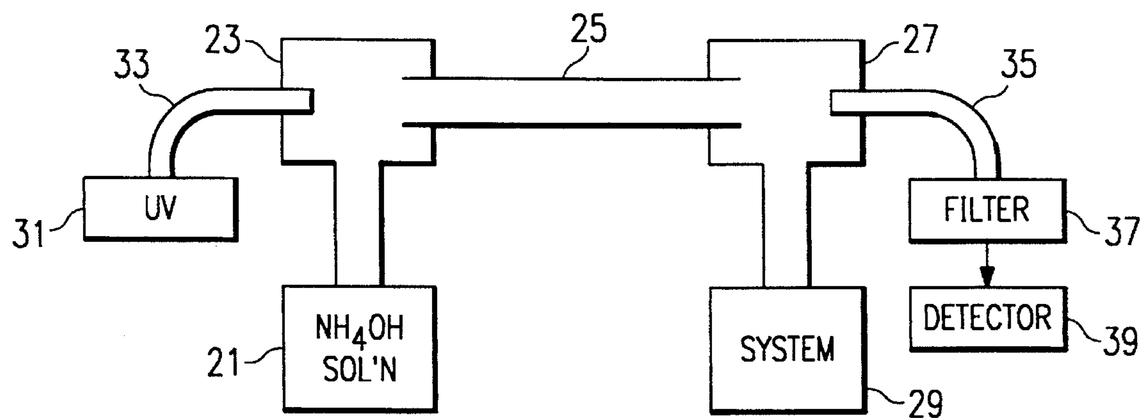
FIG. 2 is a schematic diagram of a monitoring system in accordance with a second embodiment of the invention.

Referring now to FIG. 2, there is shown a schematic diagram of a second embodiment of the invention wherein metal contamination, and primarily copper contamination, is detected and monitored on line in ammonium hydroxide solutions. Copper and other transition metals form amine complexes in the presence of dissolved ammonia. Many of these complexes, especially copper, absorb radiation in the ultraviolet or visible range. Increases in absorbance can be monitored using a spectrometer in combination with a flow cell constructed from a material inert to ammonium hydroxide, preferably fluoropolymers, and specifically perfluoroethane. The flow cell is installed directly in the distribution system or bath recirculation system, allowing non-intrusive monitoring of the transition metal content.

Ammonium hydroxide solution from an aqueous ammonium hydroxide source 21 passes through a T-fitting 23 to a first end of a perfluoroethane pipe 25 secured to the T-fitting 23. The other end of the pipe 25 is secured to a T-fitting 27 through which the ammonium hydroxide passes and then travels on to the system 29 wherein the ammonium hydroxide will be utilized. The system 29 can be, for example, a semiconductor fabrication operation. The pipe 25 is straight so that a light beam entering one end thereof along the pipe axis can exit from the other end unimpeded.

An ultraviolet light source 31, which provides ultraviolet light in the range of from about 275 to about 350 nanometers (nm), is coupled to the T-fitting 23 via a standard light conducting rod 33 to provide a beam of light passing out of the T-fitting 33 interior and along the axis of the pipe 25 to the T-fitting 27 and then to a light conducting rod 35 extending into the T-fitting 27 and along the axis of the pipe 25. The light passing through the light conducting rod 35 is filtered by a filter 37, which is a narrow band filter passing light only from about 275 to about 350 nanometers in wavelength, and removes substantially all light above and below that range. The light passing through the filter 37 impinges upon the detector 39, which detects the amount of light impinging thereon.

In operation, as ammonium hydroxide solution from the aqueous ammonium hydroxide source 31 travels to the system 39, it is constantly monitored on-line by the light beam passing from the light conducting rod 33 to the light conducting rod 35. The amount of light reaching the light conducting rod 35 is inversely proportional to the amount of transition metal, generally copper, in the pipe 35 since the light frequencies involved are selective to the transition metal complex as opposed to aqueous ammonium hydroxide. The intensity of the light arriving at rod 35 is monitored by the detector 39, the detector providing, for example, an indication of the amount of transition metal in the system with appropriate calibration, an alarm when the amount of transition metal in the system exceeds some predetermined value, a shut down of the system 39 when the amount of transition metal in the system exceeds some predetermined value, and the like.

Although the invention has been described with respect to specific preferred embodiments thereof, many variations and modifications will immediately become apparent to those skilled in the art. It is therefore the intention that the appended claims be interpreted as broadly as possible in view of the prior art to include all such variations and modifications.

We claim:

1. A method of monitoring a material flow for a contaminant therein comprising the steps of:

(a) providing a non-recirculating flow path, operable to supply a processing material to a processing station;

(b) selecting light having a wavelength or wavelength range that is selectively highly absorbed by one of the material and a material contaminant;

(c) passing through a portion of said flow path, while the material is flowing through the flow path to the processing station, a light beam comprised of said selected wavelength or wavelength range;

(d) filtering said light beam following its passage through said flow path to remove undesired wavelengths; and (e) providing an indication of material contamination from said filtered light beam.

2. The method of claim 1 wherein said material is HCl gas, said contaminant is moisture and the wavelength of said light beam is in the range of from about 1 micrometer to about 2 micrometers.

3. The method of claim 1, wherein said indication is determined from an intensity of said filtered light beam.

4. A method of monitoring material flow for a contaminant therein comprising the steps of:

(a) providing a non-recirculating flow path operable to supply a processing material to a processing station;

(b) passing through a portion of said flow path a light beam having a wavelength or wavelength range selectively highly absorbed by one of the material and a contaminant relative to the other, said material being aqueous ammonium hydroxide and said contaminant being a transition metal capable of forming a complex with ammonia, the wavelength or wavelength range of said light beam being in the range which is selectively absorbed by said complex relative to ammonium hydroxide;

(c) detecting said light beam following passage through said material and comparing said detected light beam with a reference; and (d) providing an indication of material contamination in response to the comparison.

5. The method of claim 4 further including the step of filtering light wavelengths from said light beam outside of said wavelength or wavelength range prior to step (c).

6. The method of claim 5 wherein step (d) includes the step of providing one of a quantitative indication of the contaminant, an alarm, shutting down the system to which the material being monitored is being delivered or any combination thereof.

7. The method of claim 4 wherein step (d) includes the step of providing one of a quantitative indication of the contaminant, an alarm, shutting down the system to which the material being monitored is being delivered or any combination thereof.

8. The method of claim 4 wherein said transition metal is copper.

9. A system for monitoring a material flow for a contaminant therein comprising:

(a) a non-recirculating flow path operable to supply a processing material to a processing station;

(b) a light source operable to generate a light beam and to direct said light beam through a portion of said flow path while the material travels along the flow path, said light beam having a wavelength or wavelength range that is selectively highly absorbed by one of the material and a material contaminant relative to the other;

(c) a filter operable to receive at least a portion of the light beam directed through said flow path and to remove undesired wavelengths;

(d) a detector operable to detect said portion of said light beam following filtering; and (e) an indicator operable to generate an indication of material contamination from said detected light.

10. The system of claim 9 wherein said material is HCl gas, said contaminant is moisture and the wavelength of said light beam is in the range of from about 1 micrometer to about 2 micrometers.

11. A method of monitoring a contaminant concentration in a material flow, comprising the steps off:

directing a fluid material to a processing station through a non-recirculatory flow path;

directing a light beam having a wavelength or range of wavelengths that is selectively highly absorbed by one of the materials or a material contaminant through the flow path while said material is passing through the flow path;

filtering said light beam following its passage through the flow path to remove undesired wavelengths; and detecting at least a portion of the light following filtering to provide an indication of one of the material or contaminant concentration.

12. The system of claim 11 wherein the contaminant is a transition metal.

* * * * *